(12) United States Patent
Loibner

(10) Patent No.: US 8,062,625 B2
(45) Date of Patent: Nov. 22, 2011

(54) CANCER IMMUNOTHERAPY PREDICTIVE PARAMETERS

(75) Inventor: Hans Loibner, Vienna (AT)

(73) Assignees: Wolfgang STOIBER, Gruenwald (DE); Hans LOIBNER, Vienna (AT)

(*) Notice: Subject to any disclaimer, the term of this patent is extended or adjusted under 35 U.S.C. 154(b) by 41 days.

(21) Appl. No.: 12/444,163

(22) PCT Filed: Oct. 3, 2007

(86) PCT No.: PCT/AT2007/000469
§ 371 (c)(1),
(2), (4) Date: Apr. 3, 2009

(87) PCT Pub. No.: WO2008/040044
PCT Pub. Date: Apr. 10, 2008

(65) Prior Publication Data
US 2010/0086570 A1  Apr. 8, 2010

(30) Foreign Application Priority Data

Oct. 3, 2006  (AT) ............................... A 1651/2006

(51) Int. Cl.
*A61K 49/00* (2006.01)
*G01N 33/53* (2006.01)
*G01N 33/573* (2006.01)

(52) U.S. Cl. ..................... 424/9.2; 435/7.21; 435/7.24

(58) Field of Classification Search .................. None
See application file for complete search history.

(56) References Cited

FOREIGN PATENT DOCUMENTS
WO   WO 02/38189 A1   5/2002

OTHER PUBLICATIONS

Abstract of Wheeler (Salud p'ublica de M'exico, (Jul.-Aug. 1997) 39 (4) 283-7).*
Efferson et al (Anticancer research, 2005, vol. 25, pp. 715-24).*
Bachman et al (Journal of Immunology, 2005, vol. 175, pp. 4677-4685).*
Morse et al (International Journal of Gastrointestinal Cancer, 2002, vol. 32, pp. 1-6).*
U.S. Appl. No. 12/444,316, filed Apr. 3, 2009, Loibner.
J. Atzpodien, et al., "Metastatic renal carcinoma comprehensive prognostic system", British Journal of Cancer, XP-002460745, 2003, pp. 348-353.
Piero Dalerba, et al., "Immunology and immunotherapy of colorectal cancer", Critical Reviews in Oncology/Hematology, vol. 46, XP-002461095, 2003, pp. 33-57.
F. Donskov, et al. "Monocytes and neutrophils as 'bad guys' for the outcome of interleukin-2 with and without histamine in metastatic renal cell carcinoma—results from a randomized phase II trial", British Journal of Cancer, vol. 94, XP-002460747, 2006, pp. 218-226, January.
Luca A. Fumagalli, et al., "Lymphocyte Counts Independently Predict Overall Survival in Advanced Cancer Patients: A Biomarker for IL-2 Immunotherapy", Journal of Immunotherapy, vol. 26, No. 5, XP009092899, 2003, pp. 394-402.
Himmler, et al., "A randomized placebo-controlled phase II study with the cancer vaccine candidate IGN101 in patients with epithelial cancers", Journal of Clinical Oncology, ASCO Annual Meeting Proceedings, vol. 23, No. 16S, Part I of II (Jun. 1 Supplement), 2005, 2 pages, submitting Abstract only.
Andres Riesco, "Five-Year Cancer Cure: Relation to Total Amount of Peripheral Lymphocytes and Neutrophils", Cancer, vol. 25, No. 1, Jan. 1970, pp. 135-140.
Schmidt, et al., "Elevated neutrophil and monocyte counts in peripheral blood are associated with poor survival in patients with metastatic melanoma: a prognostic model", British Journal of Cancer, vol. 93, XP-002460746, Jul. 19, 2005, pp. 273-278.
S. R. Walsh, et al., "Neutrophil-Lymphocyte Ratio as a Prognostic Factor in Colorectal Cancer" Journal of Surgical Oncology, vol. 91, No. 3, XP-002460743, 2005, pp. 181-184, Sep. 1.

* cited by examiner

*Primary Examiner* — Karen Canella
(74) *Attorney, Agent, or Firm* — Oblon, Spivak, McClelland, Maier & Neustadt, L.L.P.

(57) ABSTRACT

The invention relates to a method for predicting the efficacy of a cancer immunotherapy of an individual with respect to clinical benefit, which comprises the following steps: —providing a blood sample of said individual, —(a1) determining the number of lymphocytes in the blood of said individual, and/or (a2) determining the number of neutrophils in the blood of said individual, and —(b1) identifying the individual as having a predictive clinical benefit from the immunotherapy, if the number Of lymphocytes is below or equal to a lymphocyte baseline level of 1.4 to $1.8 \times 10^9$ per liter blood, especially below or equal to $1.6 \times 10^9$ per liter blood; or (b2) identifying the individual as having a predictive clinical benefit from the immunotherapy, if the number of neutrophils is below or equal to a neutrophil baseline level of from 4.0 to $6.0 \times 10^9$ per liter blood, especially below or equal to $5.0 \times 10^9$ neutrophils per liter blood; or (b3) identifying the individual as not having a predictive clinical benefit, if the number of lymphocytes is above a lymphocyte baseline level of 1.4 to $1.8 \times 10^9$ per liter blood, especially above $1.6 \times 10^9$ per liter blood and the number of neutrophils is above a neutrophil baseline level of from 4.0 to $6.0 \times 10^9$ per liter blood, especially above $5.0 \times 10^9$ neutrophils per liter blood.

14 Claims, 12 Drawing Sheets

CRCIV (total n=93): Predictive value of neutrophil counts at baseline for OS: IGN101 and placebo pts CRCIV with baseline neutrophils ≤ 5,0 x 10$^9$/L (n=41)

All stage IV pts (total n=134): Predictive value of lymphocyte counts at baseline for OS: IGN101 and placebo pts stage IV with baseline lymphocytes ≤ 1,6 x 10$^9$/L (n=61)

All stage IV (total n=134): Predictive value of lymphocyte or neutrophil counts for OS IGN101 and placebo pts stage IV with baseline lymphocyte counts ≤ 1,6 x 10⁹/L or baseline neutrophil counts ≤ 5,0 x 10⁹/L (n=103)

All pts (total n=234): Predictive value of baseline lymphocyte counts for OS IGN101 and placebo pts with baseline lymphocytes ≤ 1,6 x 10$^9$ / L (n=102)

CANCER IMMUNOTHERAPY PREDICTIVE PARAMETERS

The present invention relates to parameters which allow the prediction of a clinical benefit following prevention of cancer or treatment of cancer patients by cancer immunotherapies.

Investigations that allow a prediction of the efficacy of a planned therapeutic intervention for individual cancer patients are of great importance. Such measures allow to select the appropriate therapy for a certain disease condition and importantly avoid treatment and exposure of patients with probably ineffective but possibly toxic therapies. Given the substantial direct and indirect costs of many cancer therapies, predictive measures also have a major impact on health-economical issues.

The knowledge of predictive parameters is of great importance also in case of novel investigational agents. Success in clinical profiling of new therapeutics may critically depend on enrolment of those cancer patients into clinical trials that will likely benefit from this therapy. "Dilution" of clinical results by non-responding patients may lead to a negative study (e.g. no statistical significance in a controlled pivotal clinical trial), which would have been avoided if—based on the knowledge of predictive parameters—better inclusion criteria would have been used.

There are a variety of predictive parameters that allow the physician to decide which established therapy should be given to a cancer patient. Most of these parameters directly relate to the tumor, such as disease stage, spread of disease, previous therapies etc. Important predictive parameters are determinations of certain biological features of tumor cells such as the hormone receptor status for hormone-dependent cancers. For chemotherapies there is the possibility of ex-vivo testing of chemo-sensitivity of isolated tumor. For recently established targeted therapies the molecular detection of the presence of the relevant target is critical. A meanwhile famous example is the over-expression of the her2-neu receptor in breast cancer as crucial prerequisite for a successful therapy with the monoclonal anti-her2-neu antibody trastuzumab (Herceptin).

However, cancer is a disease that substantially involves constant interactions between tumor and the tumor-bearing host. There is increasing evidence that the immune system already plays a critical role in controlling early events in the recognition and destruction of first malignant cells, but importantly a proper function is also very important in later stages of the disease to control and stabilize progression (at least for a certain time). It is, however, well known that the immune system of cancer patients often is impaired due to the disease and also due to immunosuppressive therapies such as chemotherapies and radiation therapy.

It is assumed by most scientists in the field that cancer immunotherapies, and especially active immunotherapies such as cancer vaccines, rely on a proper function of the immune system as one of the key requisites for a possible clinical efficacy. In consequence, for such immunotherapies host factors and their interplay may be as important for clinical success as properties of the tumor. Therefore, certain immunological host parameters may predict the efficacy of cancer immunotherapies. This may be especially valid for cancer vaccine approaches, as these approaches are designed to act as trigger for a specific activation of the immune system to produce the pharmacologically active principle such as e.g. tumor-specific cytotoxic T-cells, tumor-specific antibodies with appropriate effector functions, and the like.

One of the well-known and general parameters of the status of the immune system is the white cell blood count enumerating various types of white blood cells. Such measurements are always performed in the course of a cancer therapy. Thus, for example, the number of neutrophils or the number of lymphocytes is always determined in cancer patients, especially when undergoing clinical trials.

These data have been correlated by some groups with the success of the cancer therapy. For example, Fumagalli et al. (J Immunother. 2003 September-October; 26(5): 394-402) reported that lymphocyte counts independently predicted overall survival in advanced cancer patients as a biomarker for IL-2 immunotherapy. In this study it was retrospectively evaluated whether lymphocytosis, in addition to clinical characteristics at baseline and to tumor objective response, may predict overall survival in metastatic renal cell carcinoma patients who received IL-2 subcutaneously (s.c.). Overall survival, clinical characteristics, tumor response, and total lymphocyte count at baseline and during the first treatment cycle of 266 advanced renal cell cancer patients, treated with 1 of 4 different firstline s.c. IL-2-based protocols, were studied using the Cox multivariate analysis. A two-step bootstrapping procedure confirmed such predictive performance. Lymphocyte count monitoring was regarded to represent a biomarker of the host response to subcutaneous IL-2 treatment useful for multimodal clinical assessment, as it predicts overall survival in advanced cancer patients independently from tumor response and from main clinical characteristics.

The purpose of the study of Atzpodien et al. (Br J. Cancer. 2003 Feb. 10; 88(3):348-53) was to identify a comprehensive prognostic system of pretreatment clinical parameters in 425 patients (pts) with metastatic renal-cell carcinoma treated with different subcutaneous (s.c.) recombinant cytokine-based home therapies in consecutive trials. Treatment consisted of (A) s.c. interferonalpha 2a (INF-alpha), s.c. interleukin-2 (IL-2) (n=102 pts), (B) s.c. IFN-alpha 2a, s.c. IL-2, and i.v. 5-fluorouracil (5-FU) (n=235 pts) or (C) s.c. IFN-alpha 2a, s.c. IL-2, and i.v. 5-FU combined with p.o. 13-cis-retinoic acid (13cRA) (n=88 pts). Kaplan-Meier survival analysis, log-rank statistics, and Cox regression analysis were employed to identify risk factors and to create a multiple risk factor model. The following pretreatment risk factors were identified by univariate analysis: (1) three and more metastatic sites, (2) presence of liver, lymph node or bone metastases, (3) neutrophil count > or =6500 cells microl (−1), (4) serum lactate dehydrogenase level (LDH) > or =220 U 1 (−1), and (5) serum C-reactive protein level (CRP) > or =11 mg 1 (−1). Cox regression analysis with forward stepwise variable selection identified neutrophil count as the major prognostic factor (hazard ratio=1.9, P<0.001), while serum levels of LDH and CRP, time between diagnosis of tumor and onset of metastatic disease, number of metastatic sites, and bone metastases were significant but somewhat less important prognostic variables within the multiple risk factor model (hazard ratio < or =1.5). Schmidt et al. (Brit. J. Cancer 93 (2005), 273-278) report that elevated neutrophil and monocyte counts in peripheral blood are associated with poor survival in patients with metastatic melanoma receiving IL-2-based immunotherapy.

It is an object of the present invention to provide objective immunological parameters measured at baseline (for clinical trials: preferably before first treatment of enrolled patients) that have a predictive value for a clinical benefit of cancer immunotherapies, especially regarding overall survival (OS). It is, in consequence, also an object of the present invention to provide methods for the pre-selection of cancer patients who will experience a clinical benefit following immunotherapies. These parameters should be easily detectable and manageable.

Therefore, the present invention provides a method for predicting the efficacy of a cancer immunotherapy of an individual with respect to clinical benefit, this method comprising the following steps:

providing a blood sample of said individual,
(a1) determining the number of lymphocytes in the blood of said individual and/or
(a2) determining the number of neutrophils in the blood of said individual and
(b1) identifying the individual as having a predictive clinical benefit from the immunotherapy, if the number of lymphocytes is below or equal to a lymphocyte baseline level of 1.4 to $1.8 \times 10^9$ per liter blood, especially below or equal to $1.6 \times 10^9$ per liter blood; or
(b2) identifying the individual as having a predictive clinical benefit from the immunotherapy, if the number of neutrophils is below or equal to a neutrophil baseline level of from 4.0 to $6.0 \times 10^9$ per liter blood, especially below or equal to $5.0 \times 10^9$ neutrophils per liter blood; or
(b3) identifying the individual as not having a predictive clinical benefit, if the number of lymphocytes is above a lymphocyte baseline level of 1.4 to $1.8 \times 10^9$ per liter blood, especially above $1.6 \times 10^9$ per liter blood and the number of neutrophils is above a neutrophil baseline level of from 4.0 to $6.0 \times 10^9$ per liter blood, especially above $5.0 \times 10^9$ neutrophils per liter blood.

According to the present invention, it was surprisingly determined that lymphocyte numbers and neutrophil numbers in individuals (e.g. healthy persons to whom a tumor vaccination is given or patients which already suffer from a tumor disease) could be efficient predictive markers for clinical benefits of a cancer immunotherapy, if baselines are considered which are usually within the "normal" values of individuals. It is clear that tumor patients which have already a lymphocyte or neutrophil number within pathological ranges have a bad prediction for clinical benefit in general. However, the present invention makes use of a significant difference in prediction of a treatment within the physiological range of lymphocyte numbers and neutrophil numbers or combinations of these numbers.

Usually, neutrophil numbers within 1.7 and $7.5 \times 10^9$ per liter blood, lymphocyte numbers within 1.2 and $4.5 \times 10^9$ per liter blood, or leukocyte numbers within 4 and $10 \times 10^9$ per liter blood, are regarded as physiological ("normal"). Pathological values differ from source to source, e.g. neutropenia is reported to be associated with less than $1 \times 10^9$ neutrophils; severe neutropenia is associated with less than $0.5 \times 10^9$ neutrophils. Lymphopenia is associated with less than $1 \times 10^9$ lymphocytes per liter blood; leukopenia with less than $4 \times 10^9$ leukocytes per liter blood. According to the present invention, patients with a number of lymphocytes or neutrophils within the physiological range are contemplated, i.e. with at least $0.5 \times 10^9$ lymphocytes or neutrophils per liter blood, preferably with at least $1 \times 10^9$ lymphocytes or neutrophils per liter blood. This does not exclude transiently artificially reduced levels of lymphocytes or neutrophils within the course of the present invention to be excluded from the preferred embodiments of this invention.

Within the present invention certain critical baselines for lymphocytes or neutrophils numbers (which are within the physiological range) are contemplated, for example to define a low neutrophil number or a low lymphocyte number; or combinations of these values, such as the neutrophils or lymphocytes low low value (NOL-LL).

Specifically the parameter NOL-LL (low neutrophils or low lymphocytes for a good prediction for the treatment) is a surprising result, because although it is in principle beneficial for any patient to have e.g. a high lymphocyte number, in the case of prediction of efficacy of a cancer immunotherapy, the opposite is true: in terms of prediction of clinical benefit it is beneficial if lymphocytes or neutrophils are low. Even if only one of lymphocytes or neutrophils are low (and the other number is high) prediction is positive. Only if both the lymphocyte numbers and neutrophil numbers are high, prediction for efficacy of the treatment is not good. Since neutrophils represent usually around 70% of total leukocytes, the subject matter of the present invention also relates to methods as disclosed herein, where instead of neutrophils or lymphocytes total leukocytes are contemplated, optionally with a correction factor of (around) 70%, e.g. instead of 4.0 to 6.0, especially $5.0 \times 10^9$ neutrophils per liter blood, one could also use 6.5 to 8.5, especially $7.5 \times 10^9$ leukocytes per liter blood. However, there is a likelihood that a certain amount of significance is lost, if one relies on the total leukocyte number instead of neutrophil counts.

The present invention allows a statistically significant prediction of the efficacy of the cancer immunotherapy. The clinical benefit according to the present invention may be defined in various established ways in tumor medicine. For example, definition is proper if based on time-to-event measurements (against a control group):

Improvement in overall survival (fully accepted by all oncologists and regulatory authorities)

Improvement in relapse-free survival (when no clinically evident tumor mass is present; i.e. after surgery; =adjuvant setting)

Improvement in progression-free survival (time until disease is progressing, based on defined measurable increase in tumor mass).

Benefit is often also claimed in case of an improved response rate (based on defined shrinking of a tumor mass for a certain time period). However, clinical response in terms of tumor shrinking does not necessarily improve survival parameters. According to a preferred embodiment, the improved clinical benefit is an improved overall survival time.

As already stated above, the method according to the present invention is preferably performed only with patients having a number of neutrophils or lymphocytes within "normal" ranges, i.e. usually above $1.0 \times 10^9$ of each cell type per liter blood. Preferably the number of lymphocytes is from above $1.0 \times 10^9$ to $1.6 \times 10^9$ per liter blood for a good predictive efficacy, especially from $1.2 \times 10^9$ to $1.6 \times 10^9$ per liter blood. According to a preferred embodiment, the number of neutrophils for the prediction of a good efficacy is from $1.0 \times 10^9$ to $5.0 \times 10^9$ per liter blood, especially from $1.7 \times 10^9$ to $5.0 \times 10^9$ per liter blood.

Cancer immunotherapy is based on therapeutic interventions that aim to utilize the immune system to combat malignant diseases. It can be divided into unspecific approaches and specific approaches. Unspecific cancer immunotherapy aims at activating parts of the immune system generally, such as treatment with specific cytokines known to be effective in cancer immunotherapy (e.g. IL-2, interferon's, cytokine inducers).

In contrast, specific cancer immunotherapy is based on certain antigens that are preferentially or solely expressed on cancer cells or predominantly expressed by other cells in the context of malignant disease (usually in vicinity of the tumor site). Specific cancer immunotherapy can be grouped into passive and active approaches:

In passive specific cancer immunotherapy substances with specificity for certain structures related to cancer that are derived from components of the immune system are administered to the patient. The most prominent and successful approaches are treatments with humanised or mouse/human chimeric monoclonal antibodies against defined cancer associated structures (such as Trastuzumab, Rituximab, Cetuximab, Bevacizumab, Alemtuzumab). The pharmacologically active substance exerts is activity as long as a sufficient concentration is present in the body of the patient, therefore administrations have to be repeated based on pharmacokinetic and pharmacodynamic considerations.

On the other hand, active specific cancer immunotherapy aims at antigen-specific stimulation of the patient's immune system to recognise and destroy cancer cells. Active specific cancer immunotherapy therefore, in general, is a therapeutic vaccination approach. There are many types of cancer vaccine approaches being pursued, such as vaccination with autologous or allogeneic whole tumor cells (in most cases genetically modified for better immune recognition), tumor cell lysates, whole tumor associated antigens (produced by means of genetic engineering or by chemical synthesis), peptides derived from protein antigens, DNA vaccines encoding for tumor associated antigens, surrogates of tumor antigens such as anti-idiotypic antibodies used as vaccine antigens, and the like. These manifold approaches are usually administered together with appropriate vaccine adjuvants and other immunomodulators in order to elicit a quantitatively and qualitatively sufficient immune response (many novel vaccine adjuvant approaches are being pursued in parallel with the development of cancer vaccines). Another set of cancer vaccine approaches relies on manipulating dendritic cells (DC) as the most important antigen presenting cell of the immune system. For example, loading with tumor antigens or tumor cell lysates, transfection with genes encoding for tumor antigens and in-vivo targeting are suitable immunotherapies according to the present invention.

Consequently, preferred cancer immunotherapies according to the present invention are selected from the group consisting of unspecific cancer immunotherapy, preferably treatment with cytokines, especially treatment with interleukin-2 (IL-2), interferons or cytokine inducers, tumor antigen-specific active immunotherapy and tumor antigen-specific passive immunotherapy, or combinations thereof. It is specifically preferred that said cancer immunotherapy is a tumor antigen-specific active or passive immunotherapy and that said individual suffers from a tumor which is associated with said tumor antigen or antigens.

According to a preferred embodiment, the cancer immunotherapy according to the present invention includes administration of an immunogenic antibody. Such antibodies are preferably based on one or more tumor antigens being specific for the cancer to be treated. Preferred immunogenic antibodies to be used according to the present invention are for example described in EP 0 528 767, EP 0 644 947, EP 1 140 168 and EP 1 230 932. A preferred antibody used for active immunotherapy is an anti-EpCAM antibody as described in WO 00/41722 or WO 2004/091655. A specifically preferred antibody is the antibody IGN101, an anti-EpCAM anti-body described e.g. in WO 00/41722. IGN 101 is a ready-to-use therapeutic vaccine that triggers an immune response to EpCAM (epithelial cell adhesion molecule), a membrane molecule that is almost always expressed—and often over-expressed—on epithelial cancer cells and that mediates self-adhesion. The vaccine antigen in IGN 101 is an immunogenic murine monoclonal antibody that structurally mimics certain EpCAM epitopes but also itself binds to EpCAM.

The methods according to the present invention are generally applicable for all types of tumors or tumor patients, specifically for tumor patients undergoing cancer immunotherapy. The present invention is therefore specifically suited for solid tumors, especially for tumors of the colorectal system. The present method is surprisingly suitable for tumors which are non-immunogenic tumors (i.e. tumors with low frequency of spontaneous remission; in contrast to immunogenic tumors, such as melanoma or renal cell carcinoma). Preferred tumors for the method according to the present invention are tumors which are non-immunogenic tumors (and have therefore not a direct correlation to white blood cells), especially epithelial tumors. These preferred tumors have an extremely low likelihood for spontaneous remission mainly because these tumors are more "hidden" to the immune system. Examples of preferred tumors according to the present invention are breast cancer, lung cancer, cancer in the stomach, pancreas carcinoma, prostate cancer, ovarial carcinoma and colorectal cancer. The present method is preferably applied for patients with colorectal cancer.

Preferably, the prediction is made of a tumor patient in stage III or IV of said tumor, classified according to the American Joint Committee on Cancer Manual for Staging Cancer, $6^{th}$ Edition (2002), especially a tumor patient in stage IV.

The neutrophil or lymphocyte number may also be adjusted to a level for predictive benefit if the original level of the patient does not indicate a prediction for improved benefit. With such suitable methods it is possible to modulate lymphocyte values or neutrophil values in peripheral blood e.g. to below or equal to $1.6 \times 10^9$ or below or equal to $5.0 \times 10^9$ per liter blood, respectively. Such a transient modulation of the WBC counts of cancer patients could e.g. be done immediately before start of cancer therapy, especially before cancer immunotherapy (against all common understanding of the problems caused by a damaged immune system for cancer vaccination) and may then lead to a survival benefit. As stated above, this could be achieved by several means:

Apheresis techniques to transiently reduce lymphocyte and neutrophil counts

Radiation therapies to transiently reduce lymphocyte and neutrophil counts

Pre-treatment with agents that reduce the number of lymphocytes (and neutrophils), such as chemotherapeutic drugs, monoclonal antibodies against lymphocyte markers (e.g. OKT-3, antiCD25 Mabs), immunomodulatory drugs, cytokines or mixtures thereof in an amount to effectively bring the lymphocyte/neutrophil number to the desired level for prediction of benefit.

Therefore, it is preferred that said individual is an individual who had received a lymphocyte reduction treatment, preferably selected from one or more of lymphocyte reducing apheresis, radiation therapy or administration of lymphocyte reducing agents, especially of chemotherapeutic drugs, monoclonal antibodies against lymphocyte markers, immunomodulatory drugs, cytokines or mixtures thereof, or that said individual is an individual who had received a neutrophil reduction treatment, preferably selected from one or more of neutrophil reducing apheresis, radiation therapy or administration of neutrophil reducing agents, especially of chemotherapeutic drugs, monoclonal antibodies against neutrophil markers, immunomodulatory drugs, cytokines or mixtures thereof.

The individual for whom a prediction is established is preferably a healthy individual with a genetic or behavioural risk of developing a tumor being associated with said tumor antigen. For such individuals a prevention of the tumor disease is critical and a successful active immunisation is highly beneficial for these persons.

In a preferred embodiment according to the present invention, a method for identifying the prediciton for improved clinical benefit of an individual suffering from a tumor is provided which comprises providing a blood sample of said individual,
- (a1) determining the number of lymphocytes in the blood of said individual and
- (a2) determining the number of neutrophils in the blood of said individual and
- (b1) identifying the individual as having a predictive clinical benefit, if the number of lymphocytes is below or equal to a lymphocyte baseline level of 1.4 to $1.8 \times 10^9$ per liter blood, especially below or equal to $1.6 \times 10^9$ per liter blood (even if the number of neutrophils is above 4.0 to $6.0 \times 10^9$ per liter blood, especially above $5.0 \times 10^9$ neutrophils per liter blood); or
- (b2) identifying the individual as having a predictive clinical benefit, if the number of neutrophils is below or equal to a neutrophil baseline level of from 4.0 to $6.0 \times 10^9$ per liter blood, especially below or equal to $5.0 \times 10^9$ neutrophils per liter blood (even if the number of lymphocytes is above 1.4 to $1.8 \times 10^9$ per liter blood, especially above $1.6 \times 10^9$ per liter blood); or
- (b3) identifying the individual as not having a predictive clinical benefit, if the number of lymphocytes is above a lymphocyte baseline level of 1.4 to $1.8 \times 10^9$ per liter blood, especially above $1.6 \times 10^9$ per liter blood and the number of neutrophils is above a neutrophil baseline level of from 4.0 to $6.0 \times 10^9$ per liter blood, especially above $5.0 \times 10^9$ neutrophils per liter blood.

According to another aspect, the present invention also relates to a method for preventing or treating tumor diseases in an individual comprising the steps of determining whether the number of lymphocytes in the blood of said individual is above or below or equal to a lymphocyte baseline level of from 1.4 to $1.8 \times 10^9$ per liter blood, especially below or equal to $1.6 \times 10^9$ lymphocytes per liter blood, optionally adjusting the number of lymphocytes in the blood of said individual to a level below or equal to said lymphocyte baseline level, and administering an effective amount of a cancer immunotherapy drug to said individual, and optionally repeating these steps in subsequent treatments.

Accordingly, the present invention also relates to a method for preventing or treating tumor diseases in an individual comprising the steps of determining whether the number of neutrophils in the blood of said individual is above or below or equal to a neutrophil baseline level of from 4.0 to $6.0 \times 10^9$ neutrophils per liter blood, especially below or equal to $5.0 \times 10^9$ neutrophils per liter blood, optionally adjusting the number of neutrophils in the blood of said individual to a level below or equal to said neutrophil baseline level, and administering an effective amount of a cancer immunotherapy drug to said individual, and optionally repeating these steps in subsequent treatments.

Preferably, the cancer immunotherapy drug is a tumor antigen vaccine based on an antigen or antigens specific for said tumor disease to be treated or prevented.

Optional repeating of such administering may be carried out once, twice or more times (also up to 10 to 20 times per year is not unusual)

According to a preferred embodiment the tumor is an epithelial tumor, preferably breast cancer, lung cancer, especially Non-Small-Cell-Lung-Cancer (NSCLC), cancer in the stomach, pancreas carcinoma, prostate cancer, ovarial carcinoma or colorectal cancer, especially colorectal cancer.

Preferred individuals for the cancer immunotherapies according to the present invention are tumor patients in stage III or IV of said tumor, classified according to the American Joint Committee on Cancer Manual for Staging Cancer, $6^{th}$ Edition (2002), especially tumor patients in stage IV.

On the other hand, it is also preferred to treat a healthy individual with a genetic or behavioural risk of developing a tumor, especially a tumor being associated with said tumor antigen.

The adjustment of the number of lymphocytes may be established by a lymphocyte reduction treatment, preferably selected from one or more of lymphocyte reducing apheresis, radiation therapy or administration of lymphocyte reducing agents, especially of chemotherapeutic drugs, monoclonal antibodies against lymphocyte markers, immunomodulatory drugs, cytokines or mixtures thereof.

The adjustment of the number of neutrophils may be established by a neutrophil reduction treatment, preferably selected from one or more of neutrophil reducing apheresis, radiation therapy or administration of neutrophil reducing agents, especially of chemotherapeutic drugs, monoclonal antibodies against neutrophil markers, immunomodulatory drugs, cytokines or mixtures thereof.

Preferably, the number of lymphocytes and the number of neutrophils is adjusted to a level below or equal to each baseline level.

The present method is specifically suitable for designing and evaluating clinical trials for proving efficacy of a given tumor treatment by grouping of patients in specific groups selected and determined according to the parameters according to the present invention. According to a specific aspect, the present invention therefore also relates to a method for conducting clinical trials for a cancer immunotherapy comprising the grouping of patients into a group which has a lymphocyte number below or equal to a lymphocyte baseline level, said lymphocyte baseline level being a value from 1.4 to $1.8 \times 10^9$ lymphocytes per liter blood, especially $1.6 \times 10^9$ per liter blood, or a neutrophil number below or equal to a neutrophil baseline level, said neutrophil baseline level being a value from 4.0 to $6.0 \times 10^9$ neutrophils per liter blood, especially $5.0 \times 10^9$ per liter blood.

The invention consequently also relates to a method for conducting clinical trials for a cancer immunotherapy comprising the grouping of patients into a group which has a lymphocyte number below or equal to a lymphocyte baseline level, said lymphocyte baseline level being a value from 1.4 to $1.8 \times 10^9$ lymphocytes per liter blood, especially $1.6 \times 10^9$ per liter blood, and a neutrophil number below or equal to a neutrophil baseline level, said neutrophil baseline level being a value from 4.0 to $6.0 \times 10^9$ neutrophils per liter blood, especially $5.0 \times 10^9$ per liter blood.

According to a preferred embodiment, the group which has a lymphocyte number below or equal to said lymphocyte baseline level and/or has a neutrophil number below or equal to said neutrophil baseline level is treated with said cancer immunotherapy, especially with an antigen-specific tumor vaccine. This enables said group to receive the maximal possible clinical benefit from the cancer immunotherapy applied.

According to another aspect, the present invention also relates to a method for re-analysing the results of clinical trials for a tumor vaccine comprising a tumor antigen comprising the grouping of patients into a group which has a lymphocyte number below or equal to a lymphocyte baseline level, said lymphocyte baseline level being a value from 1.4 to $1.8 \times 10^9$ lymphocytes per liter blood, especially $1.6 \times 10^9$ per liter blood, or a neutrophil number below or equal to a neutrophil baseline level, said neutrophil baseline level being a value from 4.0 to $6.0 \times 10^9$ neutrophils per liter blood, especially $5.0 \times 10^9$ per liter blood, and re-evaluating the efficacy of the clinical trial based on this grouping based on lymphocyte or neutrophil number.

The present invention also relates to a method for re-analysing the results of clinical trials for a tumor vaccine comprising a tumor antigen comprising the grouping of patients into a group which has a lymphocyte number below or equal to a lymphocyte baseline level, said lymphocyte baseline level being a value from 1.4 to $1.8 \times 10^9$ lymphocytes per liter blood, especially $1.6 \times 10^9$ per liter blood, and a neutrophil number below or equal to a neutrophil baseline level, said neutrophil baseline level being a value from 4.0 to $6.0 \times 10^9$ neutrophils per liter blood, especially $5.0 \times 10^9$ per liter blood, and re-evaluating the efficacy of the clinical trial based on this grouping based on lymphocyte and neutrophil number.

These methods for conducting or re-analysing clinical trials have been proven to be effective in colorectal cancer trials, but are in principle applicable for all cancer trials, especially those cancers which do not primarily involve the immune system itself (malignancies of the hemapoietic system, such as e.g. in leukemias). Preferably, the tumor patients are human tumor patients in stage III or IV of said tumor, classified according to the American Joint Committee on Cancer Manual for Staging Cancer, $6^{th}$ Edition (2002), especially a tumor patient in stage IV.

The conduct or re-analysis of clinical trials is often performed with the assistance of professional firms having computerised data bases or systems for such clinical trials offered to their customers. Examples of such data bases or systems are disclosed e.g. in US 2002/0143577 A1, U.S. Pat. No. 6,820,235 B1, U.S. Pat. No. 6,904,434 B1, and many of the documents cited in these documents. The present invention therefore also relates to such data storage means used and offered in connection with clinical trials comprising a grouping of patients as defined according to the present invention (as well as the computers on which these data storage means are running or are operatable).

According to a further aspect, the present invention also relates to the use of a preparation comprising a cancer immunotherapy agent for the manufacture of a cancer immunotherapy drug for treating a tumor patient suffering from a tumor, wherein the number of lymphocytes in the blood of said tumor patient is below or equal to a lymphocyte baseline level of 1.4 to $1.8 \times 10^9$ per liter blood, especially below or equal to $1.6 \times 10^9$ per liter blood.

Consequently, the invention also relates to the use of a preparation comprising a cancer immunotherapy agent for the manufacture of a cancer immunotherapy drug for treating a tumor patient suffering from a tumor, wherein the number of neutrophils in the blood of said patient is below or equal to a neutrophil baseline level of from 4 to $6 \times 10^9$ and per liter blood, especially $5 \times 10^9$ neutrophils per liter blood.

The selection of the panel of recipients of such immunotherapies (especially active or passive tumor vaccination) has shown to be highly predictive for a successful treatment in terms of clinical benefit, such as overall survival time.

A related aspect of the present invention is represented by a method for identifying an individual as having a good predicted clinical benefit for effective tumor vaccination based on tumor antigens, said individual suffering from a tumor which is associated with said tumor antigen, comprising
providing a blood sample of said individual,
determining the number of lymphocytes or neutrophils in the blood of said individual and
identifying the individual as having a good predicted clinical benefit for effective tumor vaccination based on tumor antigens, if the number of lymphocytes in the blood of said tumor individual is below or equal to a lymphocyte vaccination baseline level of 1.4 to $1.8 \times 10^9$ per liter blood, especially below or equal to $1.6 \times 10^9$ per liter blood, or if the number of neutrophils is below or equal to a neutrophil vaccination baseline level of 4.0 to $6.0 \times 10^9$ per liter blood, especially below or equal to $5.0 \times 10^9$ per liter blood.

A preferred embodiment of this method comprises the steps of
providing a blood sample of said individual,
determining the number of lymphocytes and neutrophils in the blood of said individual and
identifying the individual as having a good predicted clinical benefit for effective tumor vaccination based on tumor antigens, if the number of lymphocytes in the blood of said tumor individual is below or equal to a lymphocyte vaccination baseline level of 1.4 to $1.8 \times 10^9$ per liter blood, especially below or equal to $1.6 \times 10^9$ per liter blood, and if the number of neutrophils is below or equal to a neutrophil vaccination baseline level of 4.0 to $6.0 \times 10^9$ per liter blood, especially below or equal to $5.0 \times 10^9$ per liter blood.

According to a preferred embodiment, the present invention relates to a method for preventing or treating tumor diseases in an individual comprising the steps of
determining whether the number of lymphocytes in the blood of said individual is above or below or equal to a lymphocyte baseline level of from 1.4 to $1.8 \times 10^9$ per liter blood, especially below or equal to $1.6 \times 10^9$ lymphocytes per liter blood,
optionally adjusting the number of lymphocytes in the blood of said individual to a level below or equal to said lymphocyte baseline level,
determining whether the number of neutrophils in the blood of said individual is above or below or equal to a neutrophil baseline level of from 4.0 to $6.0 \times 10^9$ neutrophils per liter blood, especially below or equal to $5.0 \times 10^9$ neutrophils per liter blood,
optionally adjusting the number of neutrophils in the blood of said individual to a level below or equal to said neutrophil baseline level, and
administering an effective amount of a cancer immunotherapy drug to said individual, and optionally repeating these steps in subsequent treatments.

Preferred embodiments of this method are performed as described above.

The present invention is further described in the following examples and Figs., yet without being restricted thereto.

EXAMPLES

The present investigations are based on a data set accumulated in the context of a finished and thus opened double-blind placebo controlled Phase IIb trial with the cancer vaccine IGN101 (Himmler et al., Proceedings ASCO 2005, Abstract #2555, "A randomized placebo-controlled phase II study with the cancer vaccine candidate IGN101 in patients with epithelial cancers") in patients with epithelial cancers.

Methods:

As described in the co-pending patent application of the applicant of the present invention filed on the same day as the present invention, lymphocyte and neutrophil counts (and in particular the composite parameters NOL-LH and NML) have a prognostic value for cancer patients, especially regarding overall survival. Overall leukocyte counts also have prognostic value, but, as summary parameter, act in this regard similar to neutrophil counts, since neutrophils are the main cell type of the leukocyte pool.

As for the induction of an immune response against a cancer vaccine such as IGN101 white blood cells are considered important, it was investigated and described in the following examples, whether baseline lymphocyte and/or neutrophil counts (at the time of randomization of patients, prior start of treatment) predict the efficacy of IGN101 regarding overall survival prolongation, always in direct comparison with the respective patients who were being treated with placebo. In general, analyses are based on the Intention To Treat (ITT) population. The actually used number of patients always is mentioned in the respective section. These numbers may differ to a minor extent from the ITT population as defined in the official study report, since (very few) patients with missing baseline parameters or death date information had to be omitted. Respective data were available for 234 of the 239 randomized patients.

The distribution of stages and indications was as follows:

| Patients treated with placebo (n = 118): | |
|---|---|
| Stage III: | 54 (including 1 pt stage II) |
| colon: | 23 |
| rectum: | 13 |
| NSCLC: | 10 |
| gastric: | 6 |
| other: | 2 |
| Stage IV: | 64 |
| colon: | 25 |
| rectum: | 21 |
| NSCLC: | 9 |
| gastric: | 7 |
| other: | 2 |
| Patients treated with IGN101 (n = 116): | |
| Stage III: | 46 (including 1 pt stage II) |
| colon: | 16 |
| rectum: | 16 |
| NSCLC: | 8 |
| gastric: | 5 |
| other: | v1 |
| Stage IV: | 70 |
| colon: | 16 |
| rectum: | 31 |
| NSCLC: | 10 |
| gastric: | 12 |
| other: | 1 . . . |

Figure 1:
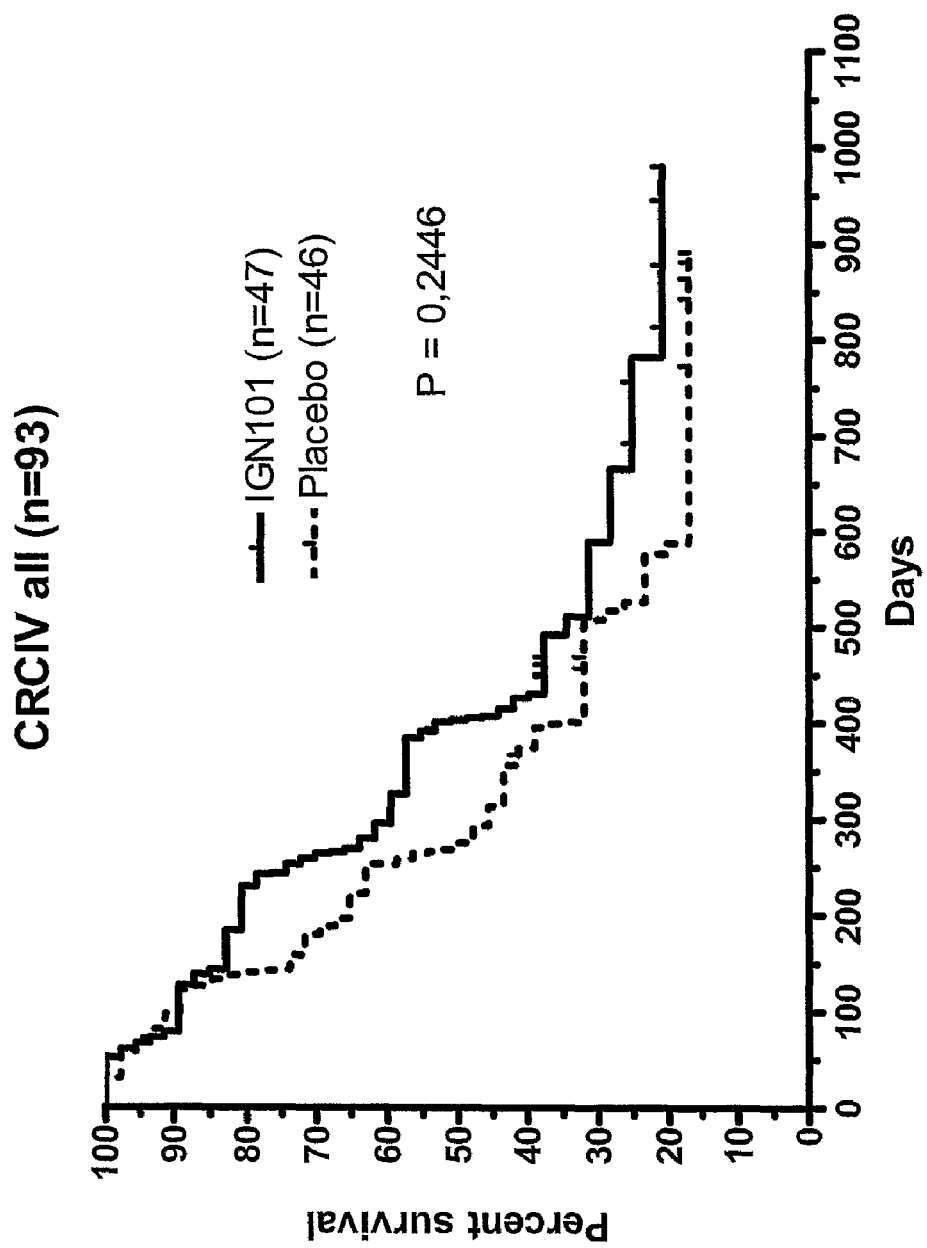
FIG. 1 shows Kaplan Meier survival curves for all stage IV colorectal cancer patients (n=93) treated with vaccine or placebo.

For the calculations and plotting of Figs. the following software programmes were used:
Tables: MS Excel
Kaplan Meier survival curves: GraphPad Prism 4
Cox'regression analysis: Internet: http://members.aol.com/johnp71/prophaz2.html Results:

1. Patients with Colo-rectal Cancer (CRC) Stage IV: Lower Lymphocyte Counts at Baseline as Predictive Marker for Efficacy The Kaplan Meier survival curves for all CRC stage IV patients without pre-selection are shown in FIG. 1. A hint for a survival prolongation of the patients treated with the vaccine compared to placebo is seen (P=0.2446).

Figure 2:
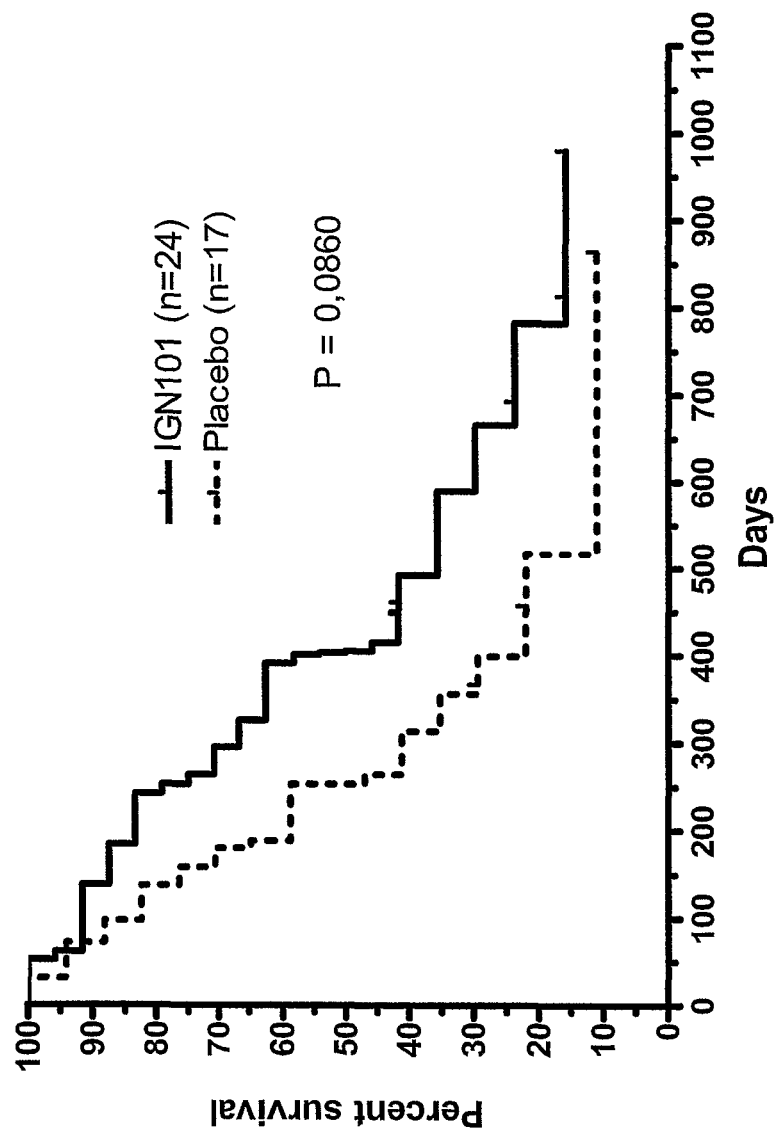
FIG. 2 shows Kaplan Meier survival curves for all stage IV colorectal cancer patients with lymphocyte counts $<1.6 \times 10^9$/L at baseline (n=41), treated with vaccine or placebo.

Next, only CRC stage IV patients with baseline lymphocyte counts <1.6×10$^9$/L and then treated with vaccine or placebo were compared regarding their overall survival. The Kaplan Meier survival curves for these patients are shown in FIG. 2. In contrast to the results obtained with all CRC IV patients, when this preselection is applied, a survival benefit close to statistical significance is seen for the patients treated with the vaccine. The median survival is 404 days (IGN101) versus 253 days (placebo), the 1-year survival is 62.5% (IGN101) versus 29.4% (placebo). The P value of 0.0860 is clearly lower than that obtained when analysing all CRC IV patients (P=0.2446). According to this analysis, CRC IV patients with lymphocyte counts <1.6×10$^9$/L mostly experience a clinical benefit following vaccination.

Figure 3:
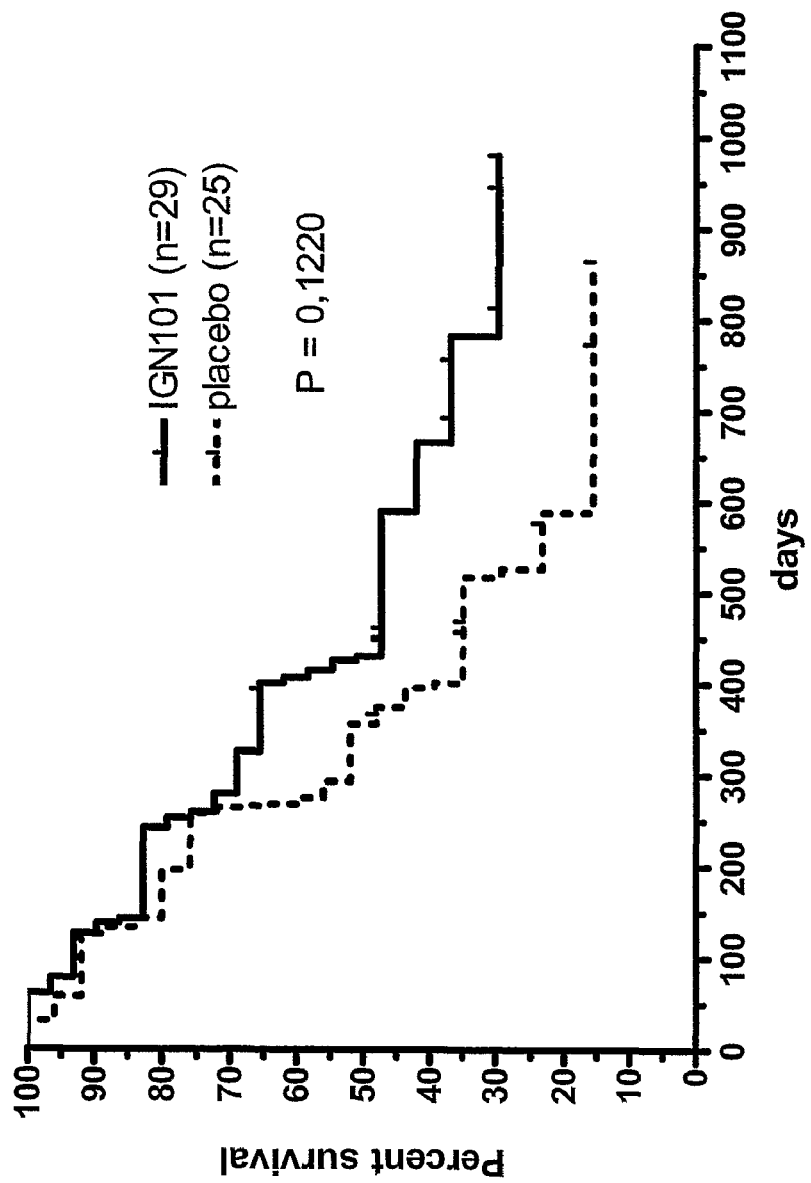
FIG. 3 shows Kaplan Meier survival curves for all stage IV colorectal cancer patients with neutrophil counts $<5.0 \times 10^9$/L at baseline (n=54), treated with vaccine or placebo.

2. Patients with Colo-rectal Cancer Stage IV: Lower Neutrophil Counts at Baseline as Predictive Marker for Efficacy Next, CRC stage IV patients with baseline neutrophil counts <5×10$^9$/L and then treated with vaccine or placebo were compared regarding their overall survival. The Kaplan Meier survival curves for these patients are shown in FIG. 3. Similar to the results described in example 1, when this pre-selection is applied, an improved survival benefit is seen for the patients treated with the vaccine compared to the results for all CRC IV patients without pre-selection (FIG. 1). The P value of 0.1220 is considerably lower than that obtained when analysing all CRC IV patients (P=0.2446).

Figure 4:
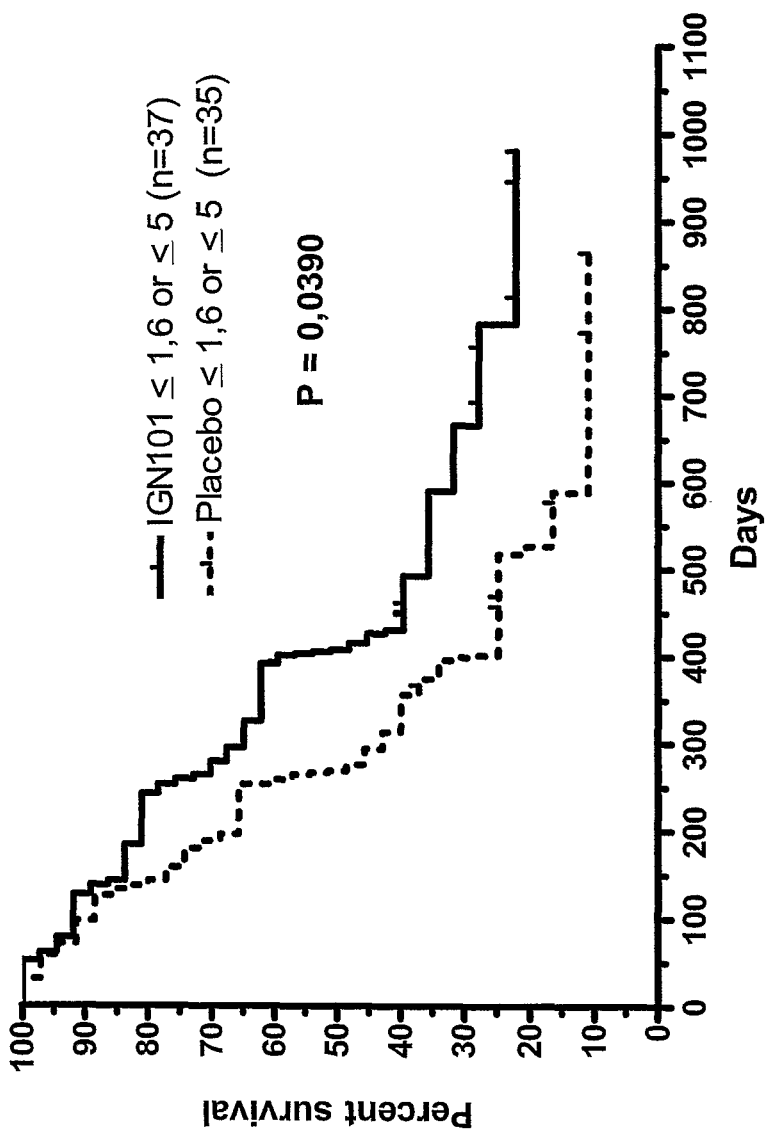
FIG. 4 shows Kaplan Meier survival curves for all stage IV colorectal cancer patients with lymphocyte counts $<1.6 \times 10^9$/L or neutrophil counts $<5.0 \times 10^9$/L at baseline (n=72), treated with vaccine or placebo.

3. Patients with Colo-rectal Cancer Stage IV: Combination of Lower Neutrophil or Lower Lymphocyte Counts at Baseline as Predictive Marker for Efficacy Since lower lymphocyte counts as well as lower neutrophil counts at baseline have a predictive value for the efficacy of IGN101 vaccination of CRC IV patients (examples 1 and 2), a combination of both parameters was also analysed. CRC IV patients presenting with baseline lymphocyte counts <1.6×$10^9$/L or baseline neutrophil counts <5×$10^9$/L and then treated with vaccine or placebo were compared regarding their overall survival. This novel composite parameter is named NOL-LL (Neutrophils Or LymphocytesLow Low). The Kaplan Meier survival curves for these patients are shown in FIG. 4. A significant survival prolongation (P=0.0390) of CRC IV patients with low lymphocyte or low neutrophil counts is seen in the vaccine group. The median survival is 407 days (IGN101) versus 268 days (placebo), the 1-year survival is 62.1% (IGN101) versus 37.1% (placebo). In contrast, a survival analysis of all CRC IV patients leads to P=0.2446 only (FIG. 1). 77.4% of all CRC IV patients belong to the group with low lymphocyte or low neutrophil counts at baseline. Thus, the selection based on NOL-LL quite precisely excludes CRC IV patients who may not benefit from immunotherapy.

Figure 5:
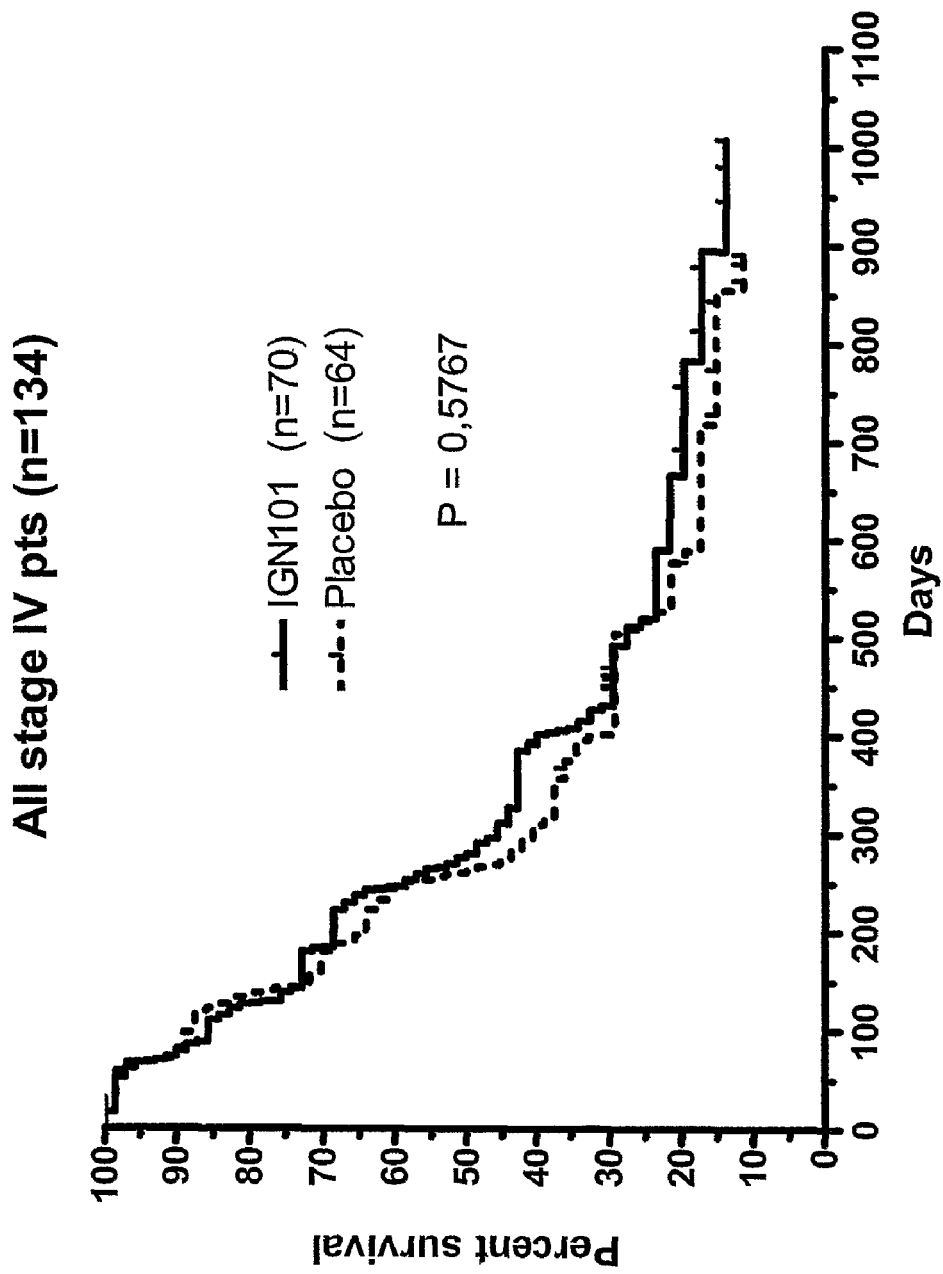
FIG. 5 shows Kaplan Meier survival curves for all stage IV cancer patients (n=134) treated with vaccine or placebo.

4. Stage IV Patients: Lower Lymphocyte Counts at Baseline as Predictive Marker for Efficacy The Kaplan Meier survival curves for all stage IV patients (distribution of indications see above) without pre-selection are shown in FIG. 5. Practically no survival prolongation of all stage IV patients treated with the vaccine compared to placebo is seen (P=0.5767).

Figure 6:
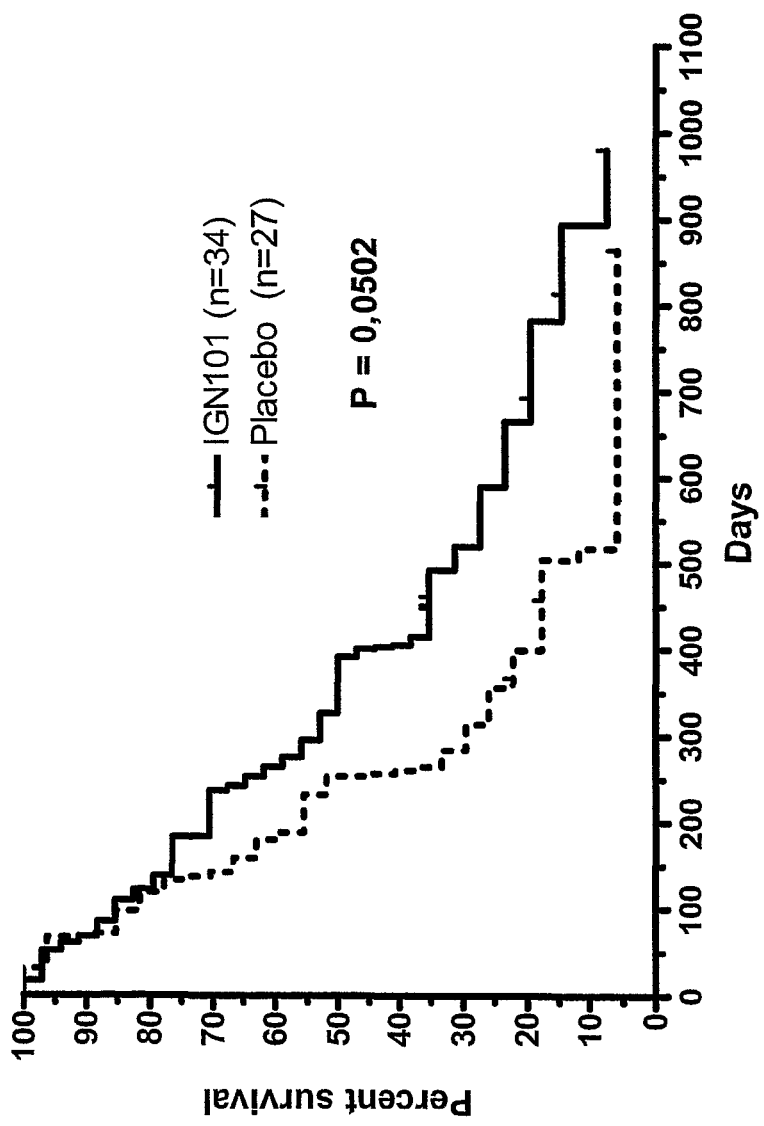
FIG. 6 shows Kaplan Meier survival curves for all stage IV cancer patients with lymphocyte counts <1.6×10$^9$/L at baseline (n=61), treated with vaccine or placebo.

Then, only stage IV patients with baseline lymphocyte counts <1.6×$10^9$/L and then treated with vaccine or placebo were compared regarding their overall survival. The Kaplan Meier survival curves for these patients are shown in FIG. 6. In contrast to the results obtained with all stage IV patients (P=0.5767), when this pre-selection is applied, a statistically significant survival benefit is seen for the patients treated with the vaccine (P=0.0502). According to this analysis and similar to the results with CRC IV patients (example 1), stage IV patients with lymphocyte counts <1.6×$10^9$/L mostly experience a clinical benefit following vaccination.

Figure 7:
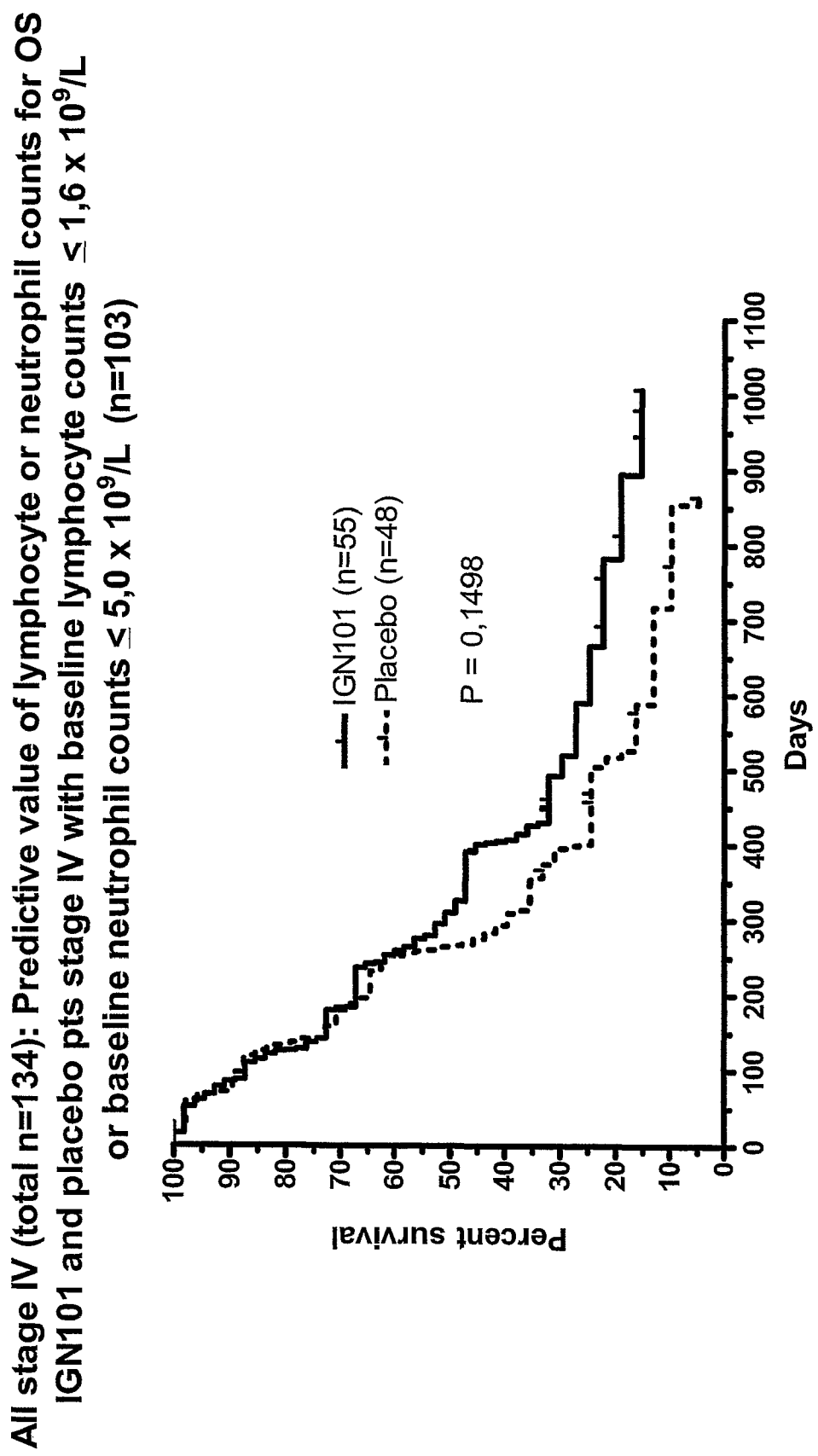
FIG. 7 shows Kaplan Meier survival curves for all stage IV cancer patients with lymphocyte counts <1.6×10$^9$/L or neutrophil counts <5.0×10$^9$/L at baseline (n=103), treated with vaccine or placebo.

5. Stage IV Patients: Combination of Lower Neutrophil or Lower Lymphocyte Counts at Baseline as Predictive Marker for Efficacy Since baseline lymphocyte counts have predictive value also for stage IV patients, the composite parameter NOL-LL combining baseline lymphocyte counts and neutrophil counts (see example 3) was also analysed for stage IV patients. The respective Kaplan Meier survival curves are shown in FIG. 7. The survival prolongation of stage IV patients with low lymphocyte or low neutrophil counts seen for the vaccine group (P=0.1498) is clearly more pronounced than that observed for all stage IV patients without pre-selection (P=0.5767, FIG. 5). Although the predictive value of NOL-LL is not as pronounced as in case of low baseline lymphocyte counts as parameter (see example 4), NOL-LL selects a greater percentage of patients into the group that has a benefit after vaccination compared to the selection by the lymphocyte count (77% versus 46% of all stage IV patients).

Figure 8:
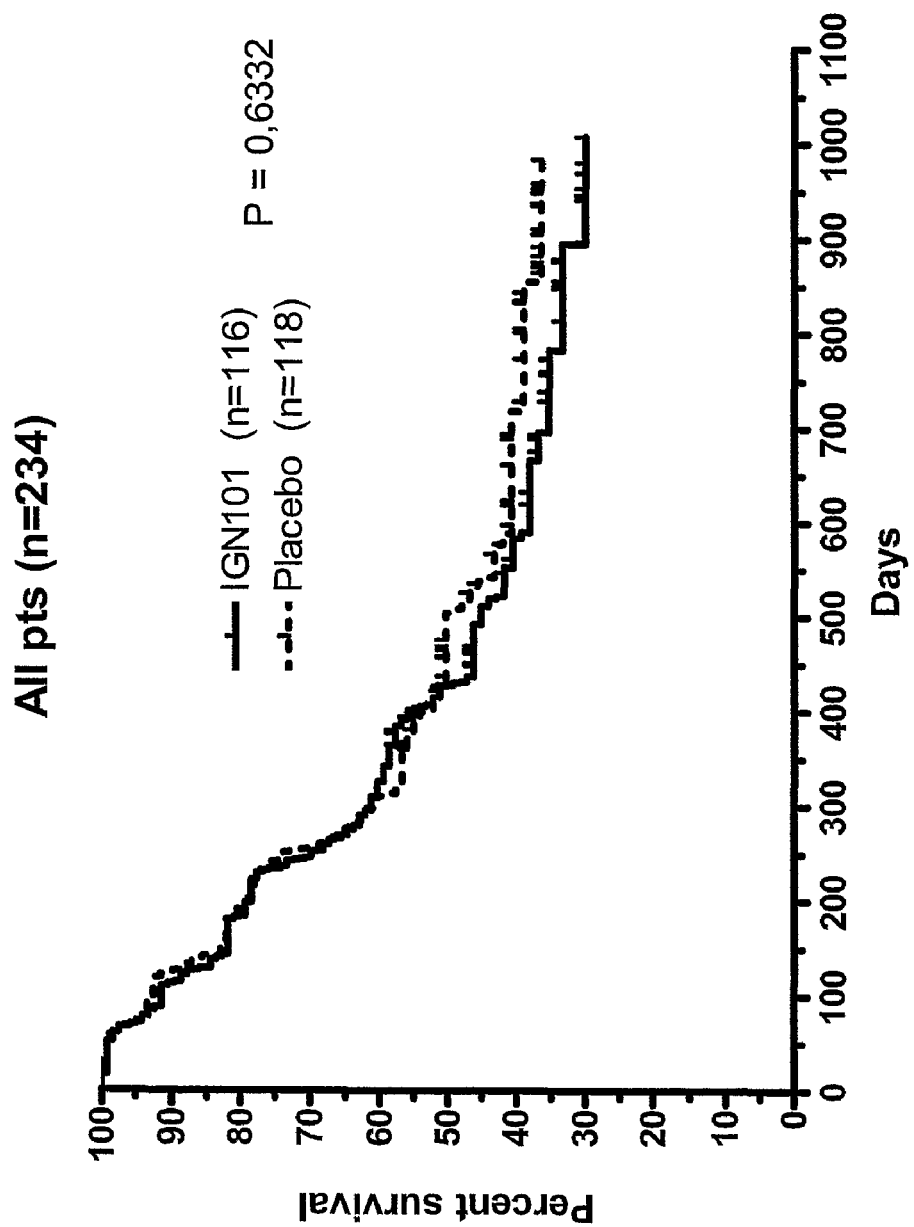
FIG. 8 shows Kaplan Meier survival curves for all cancer patients (n=234) treated with vaccine or placebo.

6. All Study Patients: Lower Lymphocyte Counts at Baseline as Predictive Marker for Efficacy The Kaplan Meier survival curves for all study patients (distribution of stages and indications see above) without pre-selection are shown in FIG. 8. No survival prolongation whatsoever is seen for patients treated with the vaccine compared to placebo (P=0.6332), there is even a very weak tendency for improved survival for placebo patients.

Figure 9:
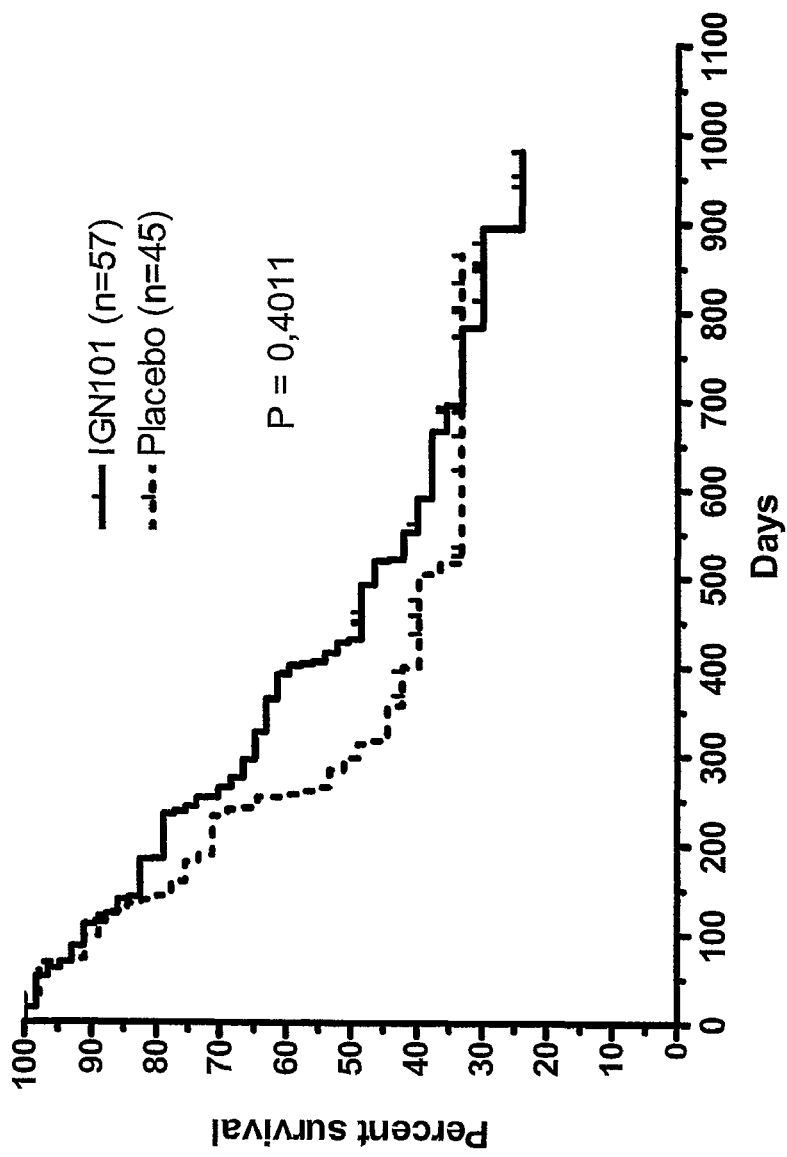
FIG. 9 shows Kaplan Meier survival curves for all cancer patients with lymphocyte counts <1.6×10$^9$/L at baseline (n=102), treated with vaccine or placebo.

Next, only those study patients with baseline lymphocyte counts <1.6×$10^9$/L and then treated with vaccine or placebo were compared regarding their overall survival. The Kaplan Meier survival curves for these patients are shown in FIG. 9. In contrast to the results obtained with all study patients, when this preselection is applied, apparently a hint for a survival benefit is seen for the patients treated with the vaccine (P=0.4011). The survival curves clearly separate but eventually collapse after approx. 2 years observation time.

7. Cox' Regression Analyses for Evaluation of the Predictive Value of Baseline Parameters Cox' regression analysis is another valuable method for the analysis of a possible predictive value of the above described baseline parameters. If treatment is the only tested predictor in such an analysis, the resulting P-values are almost identical to those obtained by Kaplan-Meier analysis using the log-rank test. However, Cox' regression analysis also allows to correct simultaneously for possible imbalances of one or several baseline factors that may influence survival results. A wellknown parameter with prognostic relevance is the Karnofski Performance Status (KPS). For example, a significant survival prolongation in the treatment group found by a Kaplan Meier survival analysis could be (partly) caused by an imbalance in KPS and not by the tested drug, if by incidence more patients with a higher KPS would be randomised to the treatment group. Such imbalances may especially play a role for smaller controlled Phase II trials and for subgroup analyses.

In view of possible bias by imbalances of prognostic factors, a series of Cox' regression analyses was performed for the CRC IV patients as homogeneous patient group, based on all CRC IV patients as well as on pre-selections obtained by applying lower baseline lymphocyte counts, lower baseline neutrophil counts and NOL-LL (all as described above). KPS as subjective parameter and the newly defined strongly prognostic parameter NML (obtained by subtraction of baseline neutrophil counts and baseline lymphocyte counts; see: co-pending Austrian patent application filed by the applicant of the present invention on the same day as the present application) as objective parameter were used as predictors and compared with the respective analyses without predictors. The resulting P values are shown in the following table:

| | log-rank | Cox no corr. | Cox with corr. |
|---|---|---|---|
| CRC IV lymphocytes ≦1.6 | 0.0860 | 0.0921 | 0.0784 |
| CRC IV neutrophils ≦5 | 0.1220 | 0.1264 | 0.1993 |
| CRC IV NOL-LL low | 0.0390 | 0.0419 | 0.0236 |
| CRC IV no pre-selection | 0.2446 | 0.2468 | 0.1519 |

The log-rank P values, as also presented in examples 1, 2 and 3 and FIGS. 1-4, and the respective P values obtained by Cox' regression analysis without correction are, as expected, almost identical. When these analyses were corrected for a possible imbalance regarding KPS and NML, the resulting P values in part were even lower, indicating indeed a certain imbalance of these prognostic factors "in favour" of the placebo group.

Furthermore, a placebo-controlled double blind clinical trial with the cancer vaccine IGN101 in 762 patients with Non-SmallCell-Lung-Cancer (NSCLC) stages Ib, II and IIIa was used to analyze above described predictive parameters. At the time of unblinding, the study was ongoing for approx.

5 years. As in this study patients were included directly after RO-resection of their lung cancer, both relapse-free and overall survival (RFS and OS) was evaluated. In consequence, the predictive parameters were both assessed regarding their prognostic value for RFS and OS. Neutrophil counts and lymphocyte counts were measured at entry for all patients.

Figure 10:
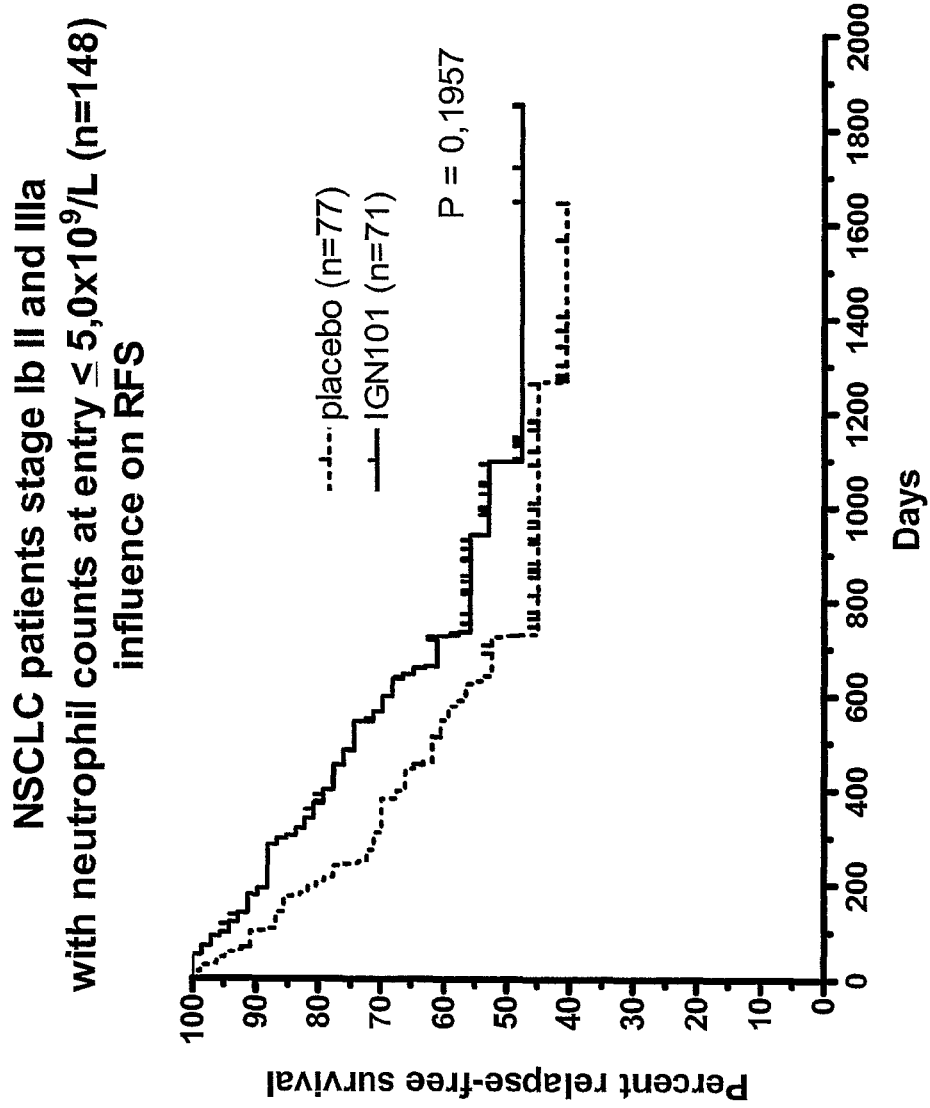
FIG. 10 shows Kaplan Meier survival curves regarding RFS for all patients with NSCLC stages Ib, II and IIIa with neutrophil counts ≦5.0×10$^9$/L at baseline (n=148), treated with vaccine or placebo.

As shown in FIG. 10, neutrophil counts at entry have a certain predictive value for RFS. NSCLC patients with lower neutrophil counts ($\leq 5 \times 10^9$/L) show a trend to improved RFS when treated with IGN101. Since most patients had substantially elevated neutrophil counts at entry due to recent surgery, only approx. 20% of patients presented with neutrophil counts $\leq 5 \times 10^9$/L.

Figure 11:
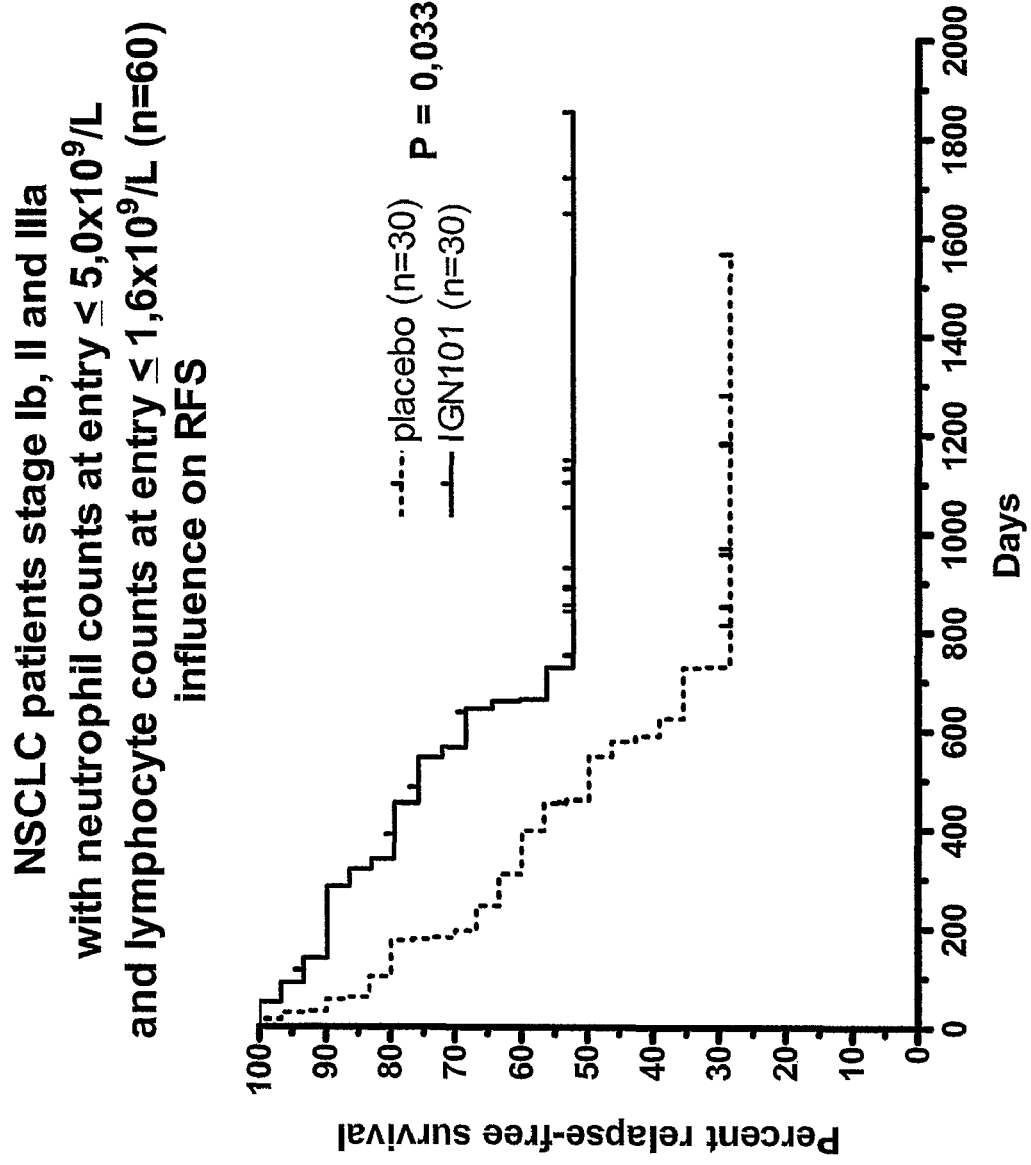
FIG. 11 shows Kaplan Meier survival curves regarding RFS for all patients with NSCLC stages Ib, II and IIIa with neutrophil counts ≦5.0×10$^9$/L at baseline and lymphocyte counts ≦1.6×10$^9$/L at baseline (n=60), treated with vaccine or placebo.
Figure 12:
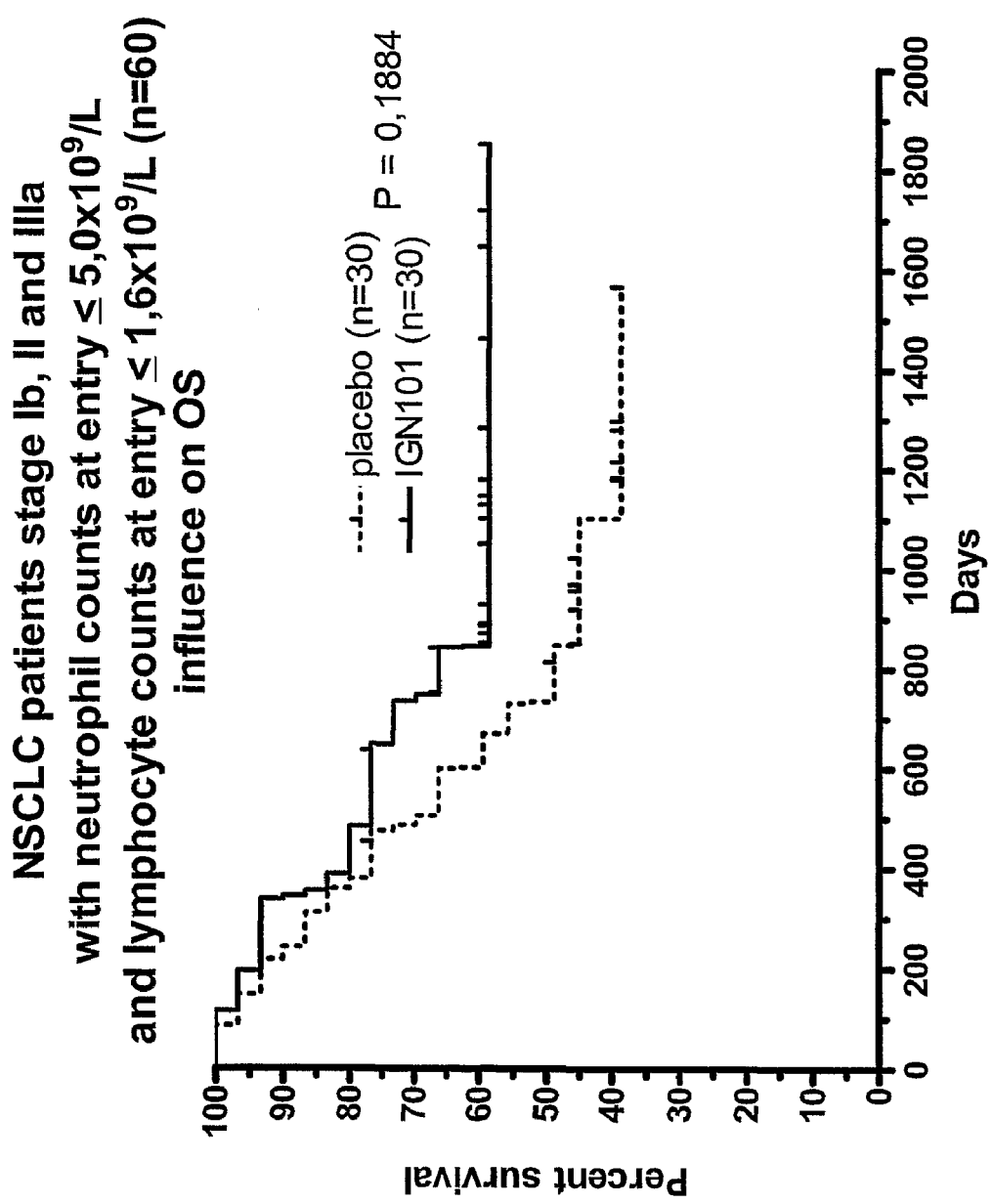
FIG. 12 shows Kaplan Meier survival curves regarding OS for all patients with NSCLC stages Ib, II and IIIa with neutrophil counts ≦5.0×10$^9$/L at baseline and lymphocyte counts ≦1.6×10$^9$/L at baseline (n=60), treated with vaccine or placebo.

As shown in FIGS. 11 and 12, NSCLC patients with lower neutrophil counts ($\leq 5 \times 10^9$/L) and lower lymphocyte counts ($\leq 1.6 \times 10^9$/L) show a significant improvement in RFS and a trend to improved OS when treated with IGN101. Obviously it is important for efficacy of IGN101 not to present with elevated neutrophils (sign of inflammation). Those NSCLC patients stage Ib, II and IIIa with rather normal neutrophil counts at entry benefit most from vaccination with IGN101 when they present also with rather low lymphocyte counts at entry, in line with the findings described above for stage IV patients.

Strikingly, neutrophil counts and lymphocyte counts measured at entry of the NSCLC patients, i.e. directly after surgery, in the early stages Ib, II and IIa, have a substantial predictive value for the efficacy of the cancer vaccine IGN101 in terms of survival parameters. It is surprising that these white blood cell counts directly after surgery of early stage NSCLC patients not only have predictive value for the efficacy of IGN101 regarding relapse-free survival, but also regarding overall survival, although death of these patients due to lung cancer usually occurs several years after surgery and therefore several years after measurement of this parameter (median time to death in this study was approx. 3 years after surgery).

The invention claimed is:

1. A method for selecting a subject for cancer immunotherapy comprising:
   determining the number of lymphocytes or neutrophils or both in the blood of a subject in need thereof;
   selecting a subject for immunotherapy when the number of lymphocytes is below or equal to a lymphocyte baseline level of $1.8 \times 10^9$ per liter blood, and/or when the number of neutrophils is below or equal to a neutrophil baseline level of $6.0 \times 10^9$ per liter blood;
   excluding a subject from immunotherapy when the number of lymphocytes is above a baseline level of $1.8 \times 10^9$ per liter blood and/or the number of neutrophils is above a baseline level of $6.0 \times 10^9$ per liter blood;
   providing immunotherapy to the selected subject; and
   not providing immunotherapy to the excluded subject.

2. The method according to claim 1, comprising selecting a subject for immunotherapy when the number of lymphocytes is below or equal to $1.4 \times 10^9$ per liter blood.

3. The method according to claim 1, comprising selecting a subject for immunotherapy when the number of lymphocytes is below or equal to $1.6 \times 10^9$ per liter blood.

4. The method according to claim 1, comprising selecting a subject for immunotherapy when the number of neutrophils is below or equal to $4.0 \times 10^9$ per liter blood.

5. The method according to claim 1, comprising selecting a subject for immunotherapy when the number of neutrophils is below or equal to $5.0 \times 10^9$ per liter blood.

6. The method according to claim 1, wherein said cancer immunotherapy is selected from the group consisting of unspecific cancer immunotherapy requiring treatment with cytokines, tumor antigen-specific active immunotherapy and tumor antigen-specific passive immunotherapy.

7. The method according to claim 1, wherein said cancer immunotherapy is a tumor antigen(s)-specific active or passive immunotherapy and wherein said subject suffers from a tumor which is associated with said tumor-specific antigen(s).

8. The method according to claim 1, wherein said tumor is an epithelial tumor.

9. The method according to claim 1, wherein the determination of lymphocyte or neutrophil number is carried out in subject who is (a) a patient having a stage III or IV tumor, (b) a patient having received a lymphocyte reduction treatment or (c) a patient having received a neutrophil reduction treatment.

10. A method for treating a tumor in a subject comprising:
    selecting a tumor bearing subject having lymphocytes greater than $1.8 \times 10^9$ per liter blood;
    adjusting the number of lymphocytes in the blood of said subject to below or equal to $1.8 \times 10^9$ per liter blood, and administering an effective amount of a cancer immunotherapy drug to said subject.

11. A method for treating a tumor in a subject comprising:
    selecting a tumor bearing subject having neutrophils greater than $6.0 \times 10^9$ per liter blood;
    adjusting the number of neutrophils in the blood of said subject to below or equal to $6.0 \times 10^9$ per liter blood, and administering an effective amount of a cancer immunotherapy drug to said subject.

12. A method for conducting a clinical trial for a cancer immunotherapy comprising:
    (a) selecting a group of patients who have a lymphocyte number below or equal to a lymphocyte baseline level of $1.8 \times 10^9$ lymphocytes per liter blood, or a neutrophil number below or equal to a neutrophil baseline level of $6.0 \times 10^9$ per liter blood;
    (b) selecting a group of patients who have a lymphocyte number below or equal to a lymphocyte baseline level of $1.8 \times 10^9$ lymphocytes per liter blood, and a neutrophil number below or equal to a neutrophil baseline level of $6.0 \times 10^9$ per liter blood;
    (c) treating each group of patients with a cancer immunotherapy agent; and
    (d) evaluating the efficacy of the cancer immunotherapy for patients in each group.

13. A method for conducting a clinical trial for a cancer immunotherapy comprising:
    selecting a group of patients who have a lymphocyte number below or equal to a lymphocyte baseline level of $1.8 \times 10^9$ lymphocytes per liter blood, or a neutrophil number below or equal to a neutrophil baseline level of $6.0 \times 10^9$ per liter blood;
    treating the group of patients with a cancer immunotherapy agent; and
    evaluating the efficacy of the cancer immunotherapy for patients in the group.

14. A method for conducting a clinical trial for a cancer immunotherapy comprising:
    selecting a group of patients who have a lymphocyte number below or equal to a lymphocyte baseline level of $1.8 \times 10^9$ lymphocytes per liter blood, and a neutrophil number below or equal to a neutrophil baseline level of $6.0 \times 10^9$ per liter blood;
    treating the group of patients with a cancer immunotherapy agent; and
    evaluating the efficacy of the cancer immunotherapy for patients in the group.

* * * * *